United States Patent [19]

Kurashina et al.

[11] Patent Number: 4,935,425
[45] Date of Patent: Jun. 19, 1990

[54] 4H-QUINOLIZIN-4-ONES FOR TREATMENT OF DISEASES ASSOCIATED WITH IMMUNOGLOBULIN E-ANTIBODY FORMATION

[75] Inventors: Yoshikazu Kurashina; Hiroshi Miyata; Den-ichi Momose, all of Matsumoto, Japan

[73] Assignee: Kissei Pharmaceutical Co., Ltd., Japan

[21] Appl. No.: 269,301

[22] Filed: Nov. 10, 1988

[30] Foreign Application Priority Data

Nov. 20, 1987 [JP] Japan .................. 62-294502
Dec. 4, 1987 [JP] Japan .................. 62-307091

[51] Int. Cl.$^5$ .................. A61K 31/50; A61K 31/505; A61K 31/495; A61K 31/435; C07D 401/14; C07D 487/06
[52] U.S. Cl. .................. 514/253; 514/233.2; 514/256; 514/306; 514/275; 544/127; 544/238; 544/328; 544/333; 544/405; 546/138
[58] Field of Search .................. 544/405, 238, 333, 127, 544/328; 514/253, 256, 306, 233.2, 275; 546/138

[56] References Cited

U.S. PATENT DOCUMENTS

4,650,804  3/1987  Kitaura et al. .................. 514/306
4,698,349  10/1987 Kitaura et al. .................. 514/306

FOREIGN PATENT DOCUMENTS

157346  10/1985  European Pat. Off. .
222482  11/1985  Japan .

OTHER PUBLICATIONS

Kobayashi et al., Yakugaku ZASSHI, 89(2), 203–208 (1969).
Kobayashi et al., Yakugaku ZASSHI, 90(2), 127—131 (1970).
Kobayashi et al., Yakugaku ZASSHI, 91(12), 1275–1278 (1971).
Kobayashi et al., Yakugaku ZASSHI, 94(1), 44–49 (1974).
Kobayashi et al., Chem. Pharm. Bull. 18(1), 124–127 (1970).
Kobayashi et al., Chem. Pharm. Bull. 21(5), 921–925 (1973).
Al-Jallo et al., Journal of Heterocyclic Chem. 10(2), 139–142 (1973).
Acheson et al., J.C.S., pp. 1143–1146, 1969.
Kappe et al., Monatish. Chem. 114, 485–493 (1983).
Kobayashi et al., Yakugaku ZASSHI, 97(9) 1039–1045 (1977).
Remers et al., CA76-85664m (1972), "Preparations and Reactions of 6-oxo-5,6,7,8-tetrahydroquinoline".
Kitaura et al., CA104-148759s (1986), "Quinolizinone Compound and Pharmaceutical Composition".
Yagimuma et al., CA106-67676a (1987), "Synthesis or Isolation of Estatin A and Estatin B and . . .".
Haraguchi et al., J. Med. Chem. 1982, 25, 1495–1499, "A Specific Inhibitor of IgE-Antibody Formation".
Acheson et al., J. Chem. Soc. (c) 1969, 1143–1146, "Addition Reactions of Heterocyclic Compounds . . .".
Ishizaka et al., The Journal of Immunology, vol. 97, pp. 75–85 (1966).

*Primary Examiner*—Cecilia Shen
*Attorney, Agent, or Firm*—Depaoli & O'Brien

[57] ABSTRACT

This invention provides novel 4H-quinolizin-4-one compounds which exhibit a selective inhibitory activity against IgE-antibody formation, and have utility for treatment of diseases associated with IgE formation in mammals, such as allergic bronchial asthma, allergic rhinitis, atopic dermatitis, hypersensitiveness, and the like.

9 Claims, No Drawings

4H-QUINOLIZIN-4-ONES FOR TREATMENT OF DISEASES ASSOCIATED WITH IMMUNOGLOBULIN E-ANTIBODY FORMATION

FIELD OF THE INVENTION

This invention relates to novel quinolizinone derivatives having utility as therapeutic agents. More particularly, this invention provides 4H-quinolizin-4-one components which exhibit selective inhibitory activities relative to IgE-antibody formation, and which have properties suitable for application as drugs for diseases associated with IgE such as allergic bronchial asthma, allergic rhinitis, atopic dermatitis, hypersensitiveness and the like.

BACKGROUND OF THE INVENTION

Several classes of immunoglobulin(s) [hereinafter referred to as Ig(s)] are well known as antibodies concerned with immune response. Most of Igs, especially immunoglobulin G (hereinafter referred to as IgG) which is one class of Igs, play an important role in self-defense mechanisms in mammals against foreign substances such as viruses, bacteria, tumours and the like.

However, immunoglobulin E (hereinafter referred to as IgE) which is another class of Igs, has been confirmed to be primarily responsible for diseases such as allergic bronchial asthma, allergic rhinitis, atopic dermatitis, hypersensitiveness, and the like (Journal of Immunology, Vol. 10, p 445. 1925, Journal of Immunology, Vol. 97, p 75, 1966). It has also been confirmed that serum concentrations of IgE in most allergic patients suffering from those diseases are higher in general than those in normal ones.

Therefore, selective inhibition of its formation might be an effective pharmacological approach for the treatment of allergy in the human. Attempts have been widely made to develop the selecive inhibitors of IgE formation. The prospective inhibitors preferably would not inhibit excessively any class of Igs except IgE for reasons mentioned above.

Up to the present time, various compounds have been reported to inhibit IgE formation in literature such as Japanese Patent Application (OPI) No. 76/87 (the term "OPI" used herein refers to an unexamined Japanese patent application); U.S. Pat. Nos. 4,395,405 and 4,691,018; British Patent Application No. 2,020,665(A) and J. Med. Chem. Vol. 25, No. 12, pages 1495–1499, 1982.

Of particular interest with respect to the present invention are publications which disclose compounds having a substituted 4H-quinolizin-4-one nucleus.

Process embodiment for production of 1-, 2- and 3-substituted 4H-quinolizin-4-one derivatives are described in Yakugaku Zasshi, Vol. 89, No. 2, pages 203–208, 1969, ibid. Vol. 90, No. 2, pages 127–131, 1970, ibid. Vol. 91, No. 12, pages 1275–1278, 1971, ibid. Vol. 94, No. 1, pages 44–49, 1974, Chem. Pharm. Bull, Vol. 18, No. 1, pages 124–127, 1970, ibid. Vol. 21, No. 5, pages 921–925, 1973, J. Heterocycl. Chem., Vol. 10, No. 2, pages 139–142, 1973, J. Chem. Soc. (c), pages 1143–1146, 1969, Monatish. Chem., Vol. 114, pages 485–493, 1983.

Anti-tumor activity of 1-, 2- and 3-substituted 4H-quinolizin-4-one derivatives of formula:

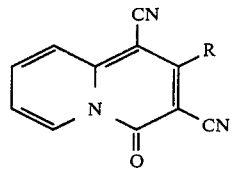

where R is methylthio, piperidino, N,N-diethyl aminoethylamino and benzylamino is disclosed in Yakugaku Zasshi, Vol 97, No. 9, pages 1039–1045, 1977.

European Patent Application No. 157346(A2) and Japanese Patent Application (OPI) No. 222482/85 which are counterparts of British Patent Application Nos. 8408292 and 8429710, filed March 30, 1984 and November 23, 1984, respectively, disclose quinolizinone derivatives having an inhibitory activity on allergies and ulcers, which derivatives correspond to the formula:

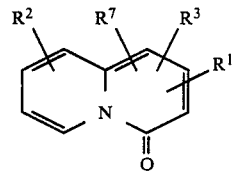

where $R^1$ is carboxy, amidated carboxy, cyano, thiocarbamoyl or tetrazolyl; $R^7$ is hydrogen or aryl; $R^2$ is hydrogen, hydroxy, lower alkyl or lower alkoxy; $R^3$ is hydrogen, hydroxy, lower alkyl, lower alkoxy, lower alkenyloxy, aryl which may have suitable substituents, arylthio, aroyl, ar(lower)alkyl, arenesulfonyl, arylamino which may have a suitable substituent or aryloxy; and $R^2$ and $R^3$ can be located at any place on the quinolizine ring and can be linked together to form $-CH_2CH_2CH_2-$, $-CH=CH-$ or $-CH=CH-CH=CH-$; and pharmaceutically acceptable salts thereof.

Japanese Patent Application (OPI) No. 77385/87 which is a counterpart of U.S. patent application Ser. No. 770,953 filed August 30, 1985, U.S. Pat. No. 4,698,349 discloses quinolizinone derivatives having an inhibitory activity on allergies and ulcers, which derivatives correspond to the formula:

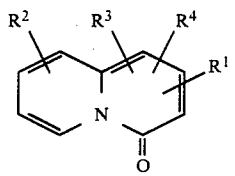

where $R^1$ is carboxy, tetrazolylcarbamoyl or amino-substituted triazolylcarbamoyl; $R^2$ is hydrogen or lower alkoxy; $R^3$ is hydrogen, aroyl, aryl, carboxy or protected carboxy; $R^4$ is hydrogen or hydroxy; with the proviso that (i) when $R^3$ is hydrogen, $R^4$ is hydroxy, (ii) when $R^3$ is aryl, $R^1$ is amino-substituted triazolylcarbamoyl and (iii) when $R^3$ is aroyl, $R^2$ is lower alkoxy; and pharmaceutically acceptable salts thereof.

U.S. Pat. No. 4,650,804 which is a counterpart of British Patent Application Nos. 8408292 and 8429710, filed March 30, 1984 and November 23, 1984, respectively, disclose quinolizinone derivatives having an inhibitory activity on allergies and ulcers, which derivatives correspond to the formula:

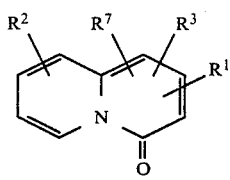

where $R^1$ is tetrazolylcarbamoyl; $R^7$ is hydrogen or aryl selected from phenyl, tolyl, xylyl, cumenyl, naphthyl and biphenylyl; $R^2$ is hydrogen, hydroxy, lower alkyl or lower alkoxy; $R^3$ is hydrogen, hydroxy, lower alkyl, lower alkoxy, lower alkenyloxy, phenyl, naphthyl, biphenylyl, phenyl having one or more substituents selected from halogen, lower alkyl and lower alkoxy, arylthio selected from phenylthio, tolylthio, xylylthio, cumenylthio, naphthylthio and biphenylylthio, aroyl selected from benzoyl, toluoyl and naphthoyl, ar(lower-)alkyl selected from phenyl(lower)alkyl, tolyl(lower)alkyl, xylyl(lower)alkyl, cumenyl(lower)alkyl, naphthyl(lower)alkyl and biphenylyl(lower)alkyl, arenesulfonyl selected from benzenesulfonyl and p-toluenesulfonyl, arylamino selected from phenylamino, naphthylamino, biphenylylamino, phenylamino having lower alkyl on the nitrogen atom or aryloxy selected from phenoxy and tolyloxy; or pharmaceutically acceptable salts thereof.

U.S. Pat. No. 4,698,349 filed August 30, 1985, disclose quinolizinone derivatives having an inhibitory activity on allergies and ulcers, which derivatives correspond to the formula:

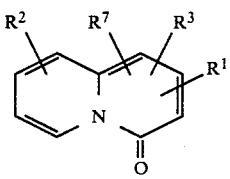

where $R^1$ is carboxy, carbamoyl, phenylcarbamoyl which may have hydroxy, cyano or thiocarbamoyl; $R^7$ is hydrogen or aryl selected from phenyl, tolyl, xylyl, cumenyl, naphthyl and biphenylyl; $R^2$ is hydrogen, hydroxy, lower alkyl or lower alkoxy; $R^3$ is hydrogen, hydroxy, lower alkyl, lower alkoxy, lower alkenyloxy, phenyl, naphthyl, biphenylyl, phenyl having one or more substituents selected from halogen, lower alkyl and lower alkoxy, arylthio selected from phenylthio, tolylthio, xylylthio, cumenylthio, naphthylthio and biphenylylthio, aroyl selected from benzoyl, toluoyl and naphthoyl, ar(lower)alkyl selected from phenyl(lower)alkyl, tolyl(lower)alkyl, xylyl(lower)alkyl, cumenyl(lower)alkyl, naphthyl(lower)alkyl and biphenylyl(lower)alkyl, arenesulfonyl selected from benzenesulfonyl and p-toluenesulfonyl, arylamino selected from phenylamino, naphthylamino, biphenylylamino, phenylamino having lower alkyl on the nitrogen atom or aryloxy selected from phenoxy and tolyloxy; or pharmaceutically acceptable salts thereof.

In none of the publications described above there is any disclosure or suggestion that novel substituted 4H-quinolizin-4-one of the type provided with the present invention might exhibit an inhibitory activity against IgE formation in mammals.

CROSS-REFERENCE TO RELATED APPLICATIONS

The subject matter of the present invention is related to that disclosed in U.S. patent application Ser. No. 147,549, filed January 25, 1988; and U.S. patent application Ser. No. 244,269, filed September 15, 1988.

SUMMARY OF THE INVENTION

Accordingly, an object of this invention is to provide novel quinolizinone derivatives which exhibit selective inhibitory activities against IgE formation when administered to human or to other mammals.

Another object of this invention is to provide pharmaceutical compositions comprising quinolizinone derivatives.

A further object of this invention is to provide methods for treatment of diseases associated with IgE formation, such as allergic bronchial asthma, allergic rhinitis, atopic dermatitis, hypersensitiveness, and the like.

Other objects, features and advantages of this invention will be apparent from the following description of the invention.

The present invention provides novel 4H-quinolizin-4-one derivatives represented by the formula:

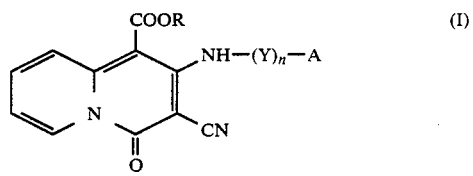

where R is an alkyl group or a phenylalkyl group; Y is an alkylene group; n is zero or 1; A is a substituted or unsubstituted 5 or 6 membered aromatic heterocyclic ring, a substituted or unsubstituted 3 to 7 membered cycloalkyl group, or a substituted or unsubstituted 5 to 7 membered saturated heterocyclic ring.

In the above and subsequent description of the present specification, the terms used in the definitions of the symbols have the following meanings.

The term "alkyl" and the "alkyl" moiety in "phenylalkyl" refer to a straight or branched alkyl group having 1 to 6 carbon atoms.

The term "alkoxy" refers to a straight or branched alkoxy group having 1 to 6 carbon atoms.

The term "alkylene" refers to a straight or branched alkylene group having 1 to 6 carbon atoms.

The term "a 5 or 6 membered aromatic heterocyclic ring" refers to a 5 or 6 membered aromatic heterocyclic ring which contains one or more hetero atoms, such as [pyrrole, furan, thiophene, imidazole, triazole, oxazole, oxadiazole, thiazole, thiadiazole] pyridine, pyrimidine, pyridazine and pyrazine.

A substituent attached to the 5 or 6 membered aromatic heterocyclic ring defined above is a radical selected from the group consisting of alkyl, amino and nitro substituents.

The term "a 3 to 7 membered cycloalkyl group" refers to a saturated or unsaturated 3 to 7 membered cycloalkyl group which may be condensed with a hydrocarbon ring.

A substituent attached to the 3 to 7 membered cycloalkyl group is a radical selected from the group consisting of alkyl and alkoxy substituents.

The term "a 5 to 7 membered saturated heterocyclic ring" refers to a 5 to 7 membered saturated heterocyclic ring containing one or more heteroatoms which may be the same or different.

When the 5 to 7 membered saturated heterocyclic ring defined above contains nitrogen atom in the ring, the ring can be connected to the quinolizine ring through the $-NH-(Y)_n-$ chain at a carbon atom or the nitrogen atom in the ring.

A substituent attached to the 5 to 7 membered saturated heterocyclic ring is a radical selected from the group consisting of alkyl and alkoxy substituents.

In another embodiment this invention provides a 4H-quinolizin-4-one compound corresponding to the formula:

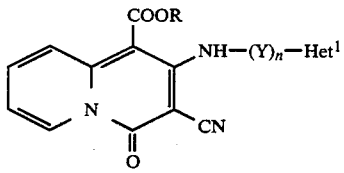

(Ia)

where R, Y and n are as previously defined; and $Het^1$ is a substituted or unsubstituted 5 or 6 membered aromatic heterocyclic group as previously defined.

In another embodiment this invention provides a 4H-quinolizin-4-one compound corresponding to the formula:

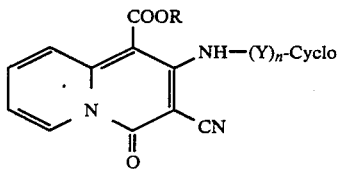

(Ib)

where R, Y and n are as previously defined; and Cyclo is a substituted or unsubstituted 3 to 7 membered cycloalkyl group as previously defined.

In another embodiment this invention provides a 4H-quinolizin-4-one compound corresponding to the formula:

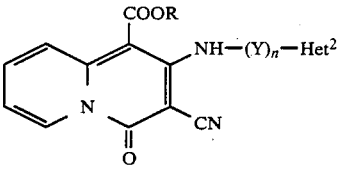

(Ic)

where R, Y and n are as previously defined; and $Het^2$ is a substituted or unsubstituted 5 to 7 membered saturated heterocyclic group as previously defined.

DETAILED DESCRIPTION OF THE INVENTION

The 4H-quinolizin-4-one derivatives of the present invention selectively inhibit the formation of IgE.

Pharmacological test data indicated that the 4H-quinolizin-4-one derivatives of formula (I) of the present invention have potential utility as drugs for diseases associated with IgE, such as allergic bronchial asthma, allergic rhinitis, atopic dermatitis, hypersensitiveness, and the like.

The 4H-quinolizin-4-one compounds of formula (I) of the present invention can be prepared according to the method described by Kobayashi et al. in Yakugaku Zasshi Vol. 89, No. 2, pp 203–208, 1969. A 4H-quinolizin-4-one derivative of the present invention corresponding to the formula:

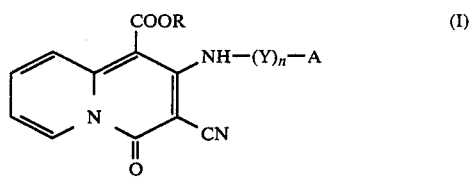

(I)

where R, Y, n and A are as previously defined, can be prepared by the reaction of a compound corresponding to the formula:

(II)

where R is as previously defined, with a compound corresponding to the formula:

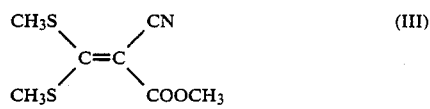

(III)

to provide an intermediate compound corresponding to the formula:

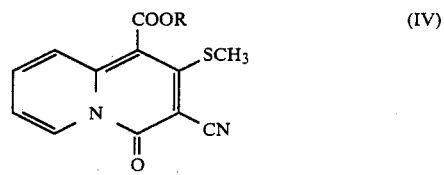

(IV)

where R is as previously defined. The intermediate compound of formula (IV) then is reacted with an amino compound corresponding to the formula:

(V)

where A, n and Y are as previously defined.

Compounds of formulae (II) and (III) for use as starting materials can be prepared as follows:

A compound of formula (II) can be prepared from 2-pyridylacetic acid according to the manner described in Compendium of Organic Synthetic Methods, Ed. by I. T. Harrison and S. Harrison, Wiley-Interscience New York, Vol. 1, pp 272–279, 1971.

A compound of formula (III) can be prepared by the reaction of methyl cyanoacetate, carbon disulfide and a dimethyl sulfate in accordance with a procedure described in Chemische Berichte, Vol. 95, pp 2861–2870, 1962.

The reaction of a compound of formula (II) with a compound of formula (III) can be conducted in accordance with the following preferred method.

A mixture of a compound of formula (II) and a compound of formula (III) in equal molar quantities is heated at 100°–120° C. for 2–10 hours, in the presence or absence of organic solvent, and then the reaction mixture is worked up by conventional procedures to produce a compound of formula (IV).

The compound of formula (IV) is reacted with a compound of formula (V) in equal molar or excess quantities at a temperature from room temperature to 140° C. for 2–48 hours, in the presence or absence of organic solvent, and the reaction mixture is worked up by conventional procedures to provide the 4H-quinolizin-4-one compound of formula (I).

The 4H-quinolizin-4-one derivatives represented by formula (I) of the present invention exhibit selective inhibitory activities on IgE formation. The inhibitory activities of the quinolizinone derivatives of formula (I) are confirmed by the determination of Igs produced in cultures of spleen cells from BALB/c mice which exhibit an adoptive secondary immune response against dinitrophenylated proteins of ascaris (DNP-As) according to a procedure described in Cellular Immunology, Vol. 58, pp 188–201, 1981. And the inhibitory activities of the quinolizinone derivative of formula (I) are further confirmed by the determination of serum concentrations of Igs in BALB/c mice which are immunized by DNP-As according to a procedure described in Immunology, Vol 21, pp 11–12, 1971.

The results obtained by these tests demonstrate that the compounds of formula (I) of the present invention inhibit IgE formation, and minimally affect the production of Igs other than IgE.

From the results obtained by these pharmacological tests, it can be expected that the compound of formula (I) of the present invention has properties suitable for application as a therapeutic agent for treatment of diseases associated with IgE in mammals.

Furthermore, the compounds of the formula (I) of the present invention also selectively inhibit IgE production in cultures of peripheral blood lymphocytes from atopic patients.

An acute toxicological test in mice shows that the compounds of formula (I) of the present invention have very low acute toxicity.

Of the 4H-quinolizin-4-one compounds represented by the formula (I), the compounds represented by the formula:

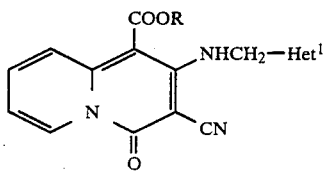

where R and Het[1] are as previously defined are preferred, and the compounds wherein Het[1] is pyrazinyl having an alkyl group on the ring as a substituent are particularly preferred. The most preferred compound is 3-cyano-1-ethoxycarbonyl-2-(5-methylpyrazinyl)methylamino-4H-quinolizin-4-one represented by the formula:

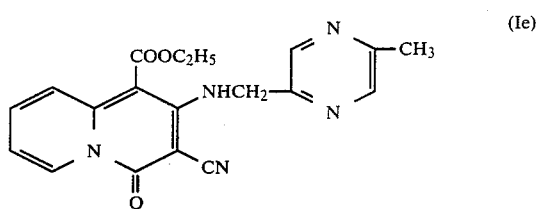

The 4H-quinolizin-4-one derivatives of the general formula (I) of the present invention can be administered in various dosage forms depending upon the intended therapy. Typical dosage forms which can be used are tablets, pills, powder, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc; binders such as gum arabic powder, tragacanth powder, and ethanol; and disintegrants such as laminaria and agar. The tablets, if desired, can be coated and made into sugar-coated tablets, gelatin-coated tablets, film-coated tablets, or tablets coated with two or more layers.

When a pharmaceutical composition is formulated into an injectable preparation, it is preferred that the resulting injectable solution and suspension are sterilized and rendered isotonic with respect to blood. In making the pharmaceutical composition into a solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active active agents.

The dosage of the quinolizinone derivatives of the present invention may be in a range from approximately 0.1 mg to 10 mg per kg of mammal weight for an oral administration, or from about 0.02 mg to 5 mg per kg of mammal weight for a parenteral administration per day in multiple doses depending upon the type of mammal disease, the severity of condition to be treated, and the like.

In another embodiment this invention provides a method for the treatment of diseases associated with IgE-antibody formation in a mammal which comprises administering an effective dosage of an invention IgE-formation-inhibiting 4H-quinolizin-4-one compound to the mammal.

In a further embodiment this invention provides a pharmaceutical composition for the treatment of diseases associated with IgE-antibody formation in a mammal, which composition contains an effective dosage of an invention IgE-formation-inhibiting 4H-quinolizin-4-one compound.

This invention is further illustrated in more detail by way of the following examples and pharmacological data.

EXAMPLE 1

3-Cyano-1-ethoxycarbonyl-2-(2-pyridylmethylamino)-4H-quinolizin-4-one (S-1)

A mixture of 1.53 g of 3-cyano-1-ethoxycarbonyl-2-methylthio-4H-quinolizin-4-one and 4.93 g of 2-aminomethylpyridine was stirred for 17 hours at room temperature. The precipitated crystals were collected by filtration and recrystallized from methanol to give 1.68 g of 3-cyano-1-ethoxycarbonyl-2-(2-pyridylmethylamino)-4H-quinolizin-4-one.

Melting point: 176.5°–177° C.
IR (KBr): 2200, 1695, 1655, 1630 cm$^{-1}$
$^1$H-NMR (CDCl$_3$): δ 1.46(t, 3H), 4.51(q, 2H), 5.22(d, 2H), 6.92(t, 1H), 7.27(t, 1H), 7.34(d, 1H), 7.51(dt, 1H), 7.72(dt, 1H), 8.25(d, 1H), 8.62(d, 1H), 9.06(d, 1H), 9.62(br, 1H)

| Elementary analysis: $C_{19}H_{16}N_4O_3$ | | | |
|---|---|---|---|
| | C % | H % | N % |
| Calcd. | 65.51 | 4.63 | 16.08 |
| Found | 65.44 | 4.68 | 15.69 |

EXAMPLE 2

The following compounds were obtained according to the same procedure as described in Example 1.

3-Cyano-1-ethoxycarbonyl-2-[2-(2-pyridyl)ethylamino]-4H-quinolizin-4-one (S-2)

Melting point: 123°–124° C.
IR (KBr): 2200, 1670, 1625 cm$^{-1}$
$^1$H-NMR (CDCl$_3$): δ 1.40(t, 3H), 3.25(t, 2H), 4.28(q, 2H), 4.41(q, 2H), 6.90(t, 1H), 7.19(dt, 1H), 7.31(d, 1H), 7.50(dt, 1H), 7.68(dt, 1H), 8.17(d, 1H), 8.57(d, 1H), 8.85(br, 1H), 9.06(d, 1H)

| Elementary analysis: $C_{20}H_{18}N_4O_3$ | | | |
|---|---|---|---|
| | C % | H % | N % |
| Calcd. | 66.29 | 5.01 | 15.46 |
| Found | 66.19 | 5.02 | 15.43 |

3-Cyano-1-(3-phenylpropoxycarbonyl)-2-[2-(2-pyridyl)ethylamino]-4H-quinolizin-4-one (S-3)

amorphous solid
IR (KBr): 2200, 1650, 1620 cm$^{-1}$
$^1$H-NMR (CDCl$_3$): δ 2.08(m, 2H), 2.73(t, 2H), 3.25(t, 2H), 4.29(q, 2H), 4.37(t, 2H), 6.91(dt, 1H), 7.12–7.33(m, 7H), 7.49(dt, 1H), 7.65(dt, 1H), 8.13(d, 1H), 8.52(d, 1H), 8.87(br, 1H), 9.06(d, 1H)

| Elementary analysis: $C_{27}H_{24}N_4O_3$ | | | |
|---|---|---|---|
| | C % | H % | N % |
| Calcd. | 71.67 | 5.35 | 12.38 |
| Found | 71.89 | 5.42 | 12.64 |

3-Cyano-1-ethoxycarbonyl-2-(2-furylmethylamino)-4H-quinolizin-4-one (S-4)

Melting point: 142°–143° C.
IR (KBr): 2200, 1670, 1630 cm$^{-1}$
$^1$H-NMR (CDCl$_3$): δ 1.39(t, 3H), 4.42(q, 2H), 5.06(d, 2H), 6.39(m, 1H), 6.43(m, 1H), 6.98(t, 1H), 7.43(m, 1H), 7.57(dt, 1H), 8.31(d, 1H), 9.00(br, 1H), 9.12(d, 1H)

| Elementary analysis: $C_{18}H_{15}N_3O_4$ | | | |
|---|---|---|---|
| | C % | H % | N % |
| Calcd. | 64.09 | 4.48 | 12.46 |
| Found | 63.88 | 4.48 | 12.32 |

3-Cyano-2-(2-furylmethylamino)-1-(3-phenylpropoxycarbonyl)-4H-quinolizin-4-one (S-5)

Melting point: 150°–151° C.
IR (KBr): 2210, 1680, 1630 cm$^{-1}$
$^1$H-NMR (CDCl$_3$): δ 2.08(m, 2H), 2.75(t, 2H), 4.37(t, 2H), 5.07(d, 2H), 6.36(m, 1H), 6.42(m, 1H), 6.99(t, 1H), 7.15–7.33(m, 5H), 7.39(m, 1H), 7.56(dt, 1H), 8.29(d, 1H), 9.03(br, 1H), 9.11(d, 1H)

| Elementary analysis: $C_{25}H_{21}N_3O_4$ | | | |
|---|---|---|---|
| | C % | H % | N % |
| Calcd. | 70.25 | 4.95 | 9.83 |
| Found | 70.13 | 5.04 | 9.60 |

3-Cyano-1-ethoxycarbonyl-2-(3-pyridylmethylamino)-4H-quinolizin-4-one (S-6)

Melting point: 124°–125° C.
IR (KBr): 2200, 1690, 1665, 1630 cm$^{-1}$
$^1$H-NMR (CDCl$_3$): δ 1.39(t, 3H), 4.39(q, 2H), 5.11(d, 2H), 7.01(t, 1H), 7.36(dt, 1H), 7.62(dt, 1H), 7.78(d, 1H), 8.33(d, 1H), 8.61(d, 1H), 8.68(d, 1H), 9.13(d, 1H), 9.21(br, 1H)

| Elementary analysis: $C_{19}H_{16}N_4O_3$ | | | |
|---|---|---|---|
| | C % | H % | N % |
| Calcd. | 65.51 | 4.63 | 16.08 |
| Found | 65.56 | 4.66 | 16.02 |

3-Cyano-1-ethoxycarbonyl-2-(4-pyridylmethylamino)-4H-quinolizin-4-one (S-7)

Melting point: 165°–168° C.
IR (KBr): 2200, 1675, 1650, 1625 cm$^{-1}$
$^1$H-NMR (CDCl$_3$): δ 1.43(t, 3H), 4.45(q, 2H), 5.11(d, 2H), 7.01(t, 1H), 7.33(d, 2H), 7.62(dt, 1H), 8.36(d, 1H), 8.64(d, 2H), 9.13(d, 1H), 9.48(br, 1H)

| Elementary analysis: $C_{19}H_{16}N_4O_3$ | | | |
|---|---|---|---|
| | C % | H % | N % |
| Calcd. | 65.51 | 4.63 | 16.08 |
| Found | 65.78 | 4.58 | 16.33 |

3-Cyano-1-ethoxycarbonyl-2-[2-(4-methylthiazol-5-yl)ethylamino]-4H-quinolizin-4-one (S-8)

Melting point: 131°–132° C.
IR (KBr): 2200, 1670, 1630 cm$^{-1}$
$^1$H-NMR (CDCl$_3$): δ 1.39(t, 3H), 2.46(brs, 3H), 3.23(t, 2H), 4.16(q, 2H), 4.39(q, 2H), 6.97(t, 1H), 7.57(dt, 1H), 8.25(d, 1H), 8.63(brs, 1H), 8.93(br, 1H), 9.10(d, 1H)

| Elementary analysis: $C_{19}H_{18}N_4O_3S$ | | | |
|---|---|---|---|
| | C % | H % | N % |
| Calcd. | 59.67 | 4.74 | 14.65 |

-continued

| Elementary analysis: C$_{19}$H$_{18}$N$_4$O$_3$S | | | |
|---|---|---|---|
| | C % | H % | N % |
| Found | 59.34 | 4.69 | 14.62 |

3-Cyano-1-ethoxycarbonyl-2-thienylmethylamino-4H-quinolizin-4-one (S-9)

Melting point: 137°–139° C.
IR (KBr): 2200, 1670, 1630 cm$^{-1}$
$^1$H-NMR (CDCl$_3$): δ 1.36(t, 3H), 4.38(q, 2H), 5.25(d, 2H), 6.95–7.03(m, 2H), 7.15(d, 1H), 7.30(d, 1H), 7.57(dt, 1H), 8.31(d, 1H), 8.95(br, 1H), 9.12(d, 1H)

| Elementary analysis: C$_{18}$H$_{15}$N$_3$O$_3$S | | | |
|---|---|---|---|
| | C % | H % | N % |
| Calcd. | 61.18 | 4.28 | 11.89 |
| Found | 60.84 | 4.35 | 11.77 |

3-Cyano-1-ethoxycarbonyl-2-(3-thienylmethylamino)-4H-quinolizin-4-one (S-10)

Melting point: 134°–135° C.
IR (KBr): 2200, 1690, 1660, 1630 cm$^{-1}$
$^1$H-NMR (CDCl$_3$): δ 1.37(t, 3H), 4.39(q, 2H), 5.09(d, 2H), 6.97(t, 1H), 7.12(d, 1H), 7.34(brs, 1H), 7.38(m, 1H), 7.56(dt, 1H), 8.29(d, 1H), 9.02(br, 1H), 9.11(d, 1H)

| Elementary analysis: C$_{18}$H$_{15}$N$_3$O$_3$S | | | |
|---|---|---|---|
| | C % | H % | N % |
| Calcd. | 61.18 | 4.28 | 11.89 |
| Found | 60.83 | 4.35 | 11.61 |

3-Cyano-1-ethoxycarbonyl-2-(2-thienylethylamino)-4H-quinolizin-4-one (S-11)

Melting point: 112°–113° C.
IR (KBr): 2200, 1675, 1630 cm$^{-1}$
$^1$H-NMR (CDCl$_3$): δ 1.38(t, 3H), 3.27(t, 2H), 4.18(q, 2H), 4.37(q, 2H), 6.90–6.98(m, 3H), 7.18(m, 1H), 7.54(dt, 1H), 8.21(d, 1H), 8.88(br, 1H), 9.09(d, 1H)

| Elementary analysis: C$_{19}$H$_{17}$N$_3$O$_3$S | | | |
|---|---|---|---|
| | C % | H % | N % |
| Calcd. | 62.11 | 4.66 | 11.44 |
| Found | 62.07 | 4.68 | 11.48 |

3-Cyano-1-ethoxycarbonyl-2-[2-(3-thienyl)ethylamino]-4H-quinolizin-4-one (S-12)

Melting point: 98°–99° C.
IR (KBr): 2200, 1680, 1660, 1630 cm$^{-1}$
$^1$H-NMR (CDCl$_3$): δ 1.38(t, 3H), 3.07(t, 2H), 4.15(q, 2H), 4.37(q, 2H), 6.93(t, 1H), 7.04(dd, 1H), 7.13(brs, 1H), 7.40(dd, 1H), 7.53(dt, 1H), 8.20(d, 1H), 8.87(br, 1H), 9.09(d, 1H)

| Elementary analysis: C$_{19}$H$_{17}$N$_3$O$_3$S | | | |
|---|---|---|---|
| | C % | H % | N % |
| Calcd. | 62.11 | 4.66 | 11.44 |
| Found | 61.88 | 4.71 | 11.41 |

2-(4-Amino-2-methylpyrimidin-5-yl)methylamino-3-cyano-1-ethoxycarbonyl-4H-quinolizin-4-one (S-13)

Melting point: 140°–144° C.
IR (KBr): 2210, 1670, 1650, 1630 cm$^{-1}$
$^1$H-NMR (CDCl$_3$): δ 1.28(t, 3H), 2.32(brs, 3H), 4.34(q, 2H), 4.71(d, 2H), 6.85(br, 2H), 7.16(t, 1H), 7.78(dt, 1H), 7.98(brs, 1H), 8.11(d, 1H), 8.25(t, 1H), 8.92(d, 1H)

| Elementary analysis: C$_{19}$H$_{18}$N$_6$O$_3$ | | | |
|---|---|---|---|
| | C % | H % | N % |
| Calcd. | 60.31 | 4.79 | 22.21 |
| Found | 60.22 | 4.83 | 22.47 |

3-Cyano-1-ethoxycarbonyl-2-pyrazinylmethylamino-4H-quinolizin-4-one (S-14)

Melting point: 185°–187° C.
IR (KBr): 2200, 1680, 1650, 1620 cm$^{-1}$ $^1$H-NMR (CDCl$_3$): δ 1.47(t, 3H), 4.50(q, 2H), 5.31(d, 2H), 6.99(t, 1H), 7.58(dt, 1H), 8.30(d, 1H), 8.59(d, 1H), 8.63(d, 1H), 8.72(brs, 1H), 9.11(d, 1H), 9.63(br, 1H)

| Elementary analysis: C$_{18}$H$_{15}$N$_5$O$_3$ | | | |
|---|---|---|---|
| | C % | H % | N % |
| Calcd. | 61.89 | 4.33 | 20.05 |
| Found | 61.84 | 4.21 | 19.68 |

3-Cyano-1-ethoxycarbonyl-2-(3-methylpyrazinyl)methylamino-4H-quinolizin-4-one (S-15)

Melting point: 198°–200° C.
IR (KBr): 2200, 1690, 1670, 1620 cm$^{-1}$
$^1$H-NMR (CDCl$_3$): δ 1.50(t, 3H), 2.66(brs, 3H), 4.55(q, 2H), 5.25(d, 2H), 6.96(t, 1H), 7.54(dt, 1H), 8.29(d, 1H), 8.46(d, 1H), 8.48(d, 1H), 9.09(d, 1H), 9.79(br, 1H)

| Elementary analysis: C$_{19}$H$_{17}$N$_5$O$_3$ | | | |
|---|---|---|---|
| | C % | H % | N % |
| Calcd. | 62.80 | 4.72 | 19.27 |
| Found | 63.01 | 4.68 | 19.46 |

3-Cyano-1-ethoxycarbonyl-2-(5-methylpyrazinyl)methylamino-4H-quinolizin-4-one (S-16)

Melting point: 183°–186° C.
IR (KBr): 2200, 1690, 1650, 1625 cm$^{-1}$
$^1$H-NMR (CDCl$_3$): δ 1.47(t, 3H), 2.60(brs, 3H), 4.49(q, 2H), 5.25(d, 2H), 6.97(t, 1H), 7.58(dt, 1H), 8.29(d, 1H), 8.50(brs, 1H), 8.59(brs, 1H), 9.10(d, 1H), 9.55(br, 1H)

| Elementary analysis: C$_{19}$H$_{17}$N$_5$O$_3$ | | | |
|---|---|---|---|
| | C % | H % | N % |
| Calcd. | 62.80 | 4.72 | 19.27 |
| Found | 62.91 | 4.69 | 19.44 |

3-Cyano-1-ethoxycarbonyl-2-(6-methylpyrazinyl)methylamino-4H-quinolizin-4-one (S-17)

Melting point: 167°–168° C.
IR (KBr): 2210, 1670, 1630 cm$^{-1}$

¹H-NMR (CDCl₃): δ 1.46(t, 3H), 2.63(brs, 3H), 4.49(q, 2H), 5.25(d, 2H), 6.96(t, 1H), 7.56(dt, 1H), 8.27(d, 1H), 8.45(brs, 1H), 8.49(brs, 1H), 9.10(d, 1H), 9.25(br, 1H)

| Elementary analysis: C₁₉H₁₇N₅O₃ | | | |
|---|---|---|---|
| | C % | H % | N % |
| Calcd. | 62.80 | 4.72 | 19.27 |
| Found | 62.40 | 4.06 | 19.07 |

3-Cyano-1-ethoxycarbonyl-2-[2-(5-nitropyridin-2-ylamino)ethylamino]-4H-quinolizin-4-one (S-18)

Melting point: 197°–199° C.
IR (KBr): 2200, 1650, 1630, 1540, 1330 cm⁻¹
¹H-NMR (CDCl₃): δ 1.28(t, 3H), 3.84(m, 2H), 3.94(m, 2H), 4.28(q, 2H), 6.58(d, 1H), 7.14(t, 1H), 7.76(dt, 1H), 8.03–8.34(m, 4H), 8.87–8.95(m, 2H)

| Elementary analysis: C₂₀H₁₈N₆O₅ | | | |
|---|---|---|---|
| | C % | H % | N % |
| Calcd. | 56.87 | 4.30 | 19.90 |
| Found | 56.42 | 4.42 | 19.77 |

3-Cyano-1-ethoxycarbonyl-2-[2-(1-methylpyrrol-2-yl)ethylamino]-4H-quinolizin-4-one (S-19)

Melting point: 145°–147° C.
IR (KBr): 2200, 1675, 1630 cm⁻¹
¹H-NMR (CDCl₃): δ 1.38(t, 3H), 3.00(t, 2H), 3.60(s, 3H), 4.13(q, 2H), 4.39(q, 2H), 6.06(m, 2H), 6.59(m, 1H), 6.92(t, 1H), 7.53(dt, 1H), 8.21(d, 1H), 8.85(br, 1H), 9.08(d, 1H)

| Elementary analysis: C₂₀H₂₀N₄O₃ | | | |
|---|---|---|---|
| | C % | H % | N % |
| Calcd. | 65.92 | 5.53 | 15.37 |
| Found | 65.90 | 5.48 | 15.64 |

3-Cyano-1-ethoxycarbonyl-2-imidazolylmethylamino-4H-quinolizin-4-one (S-20)

Melting point: 239° C. (decomp.)
IR (KBr): 2220, 1680, 1640, 1620 cm⁻¹
¹H-NMR (CDCl₃): δ 1.43(t, 3H), 4.48(q, 2H), 5.18(d, 2H), 6.98(t, 1H), 7.11(brs, 2H), 7.30(br, 1H), 7.57(dt, 1H), 8.29(d, 1H), 9.07(d, 1H), 9.40(br, 1H)

| Elementary analysis: C₁₇H₁₅N₅O₃ | | | |
|---|---|---|---|
| | C % | H % | N % |
| Calcd. | 60.53 | 4.48 | 20.76 |
| Found | 60.62 | 4.41 | 20.88 |

3-Cyano-1-ethoxycarbonyl-2-(4-imidazolylmethylamino)-4H-quinolizin-4-one (S-21)

Melting point: 245°–248° C. (decomp.)
IR (KBr): 2200, 1670, 1635 cm⁻¹
¹H-NMR (CDCl₃): δ 1.29(t, 3H), 4.35(q, 2H), 4.83(d, 2H), 7.16(m, 2H), 7.69(brs, 1H), 7.79(dt, 1H), 8.18(d, 1H), 8.63(br, 1H), 8.94(d, 1H), 12.10(br, 1H)

| Elementary analysis: C₁₇H₁₅N₅O₃ | | | |
|---|---|---|---|
| | C % | H % | N % |
| Calcd. | 60.53 | 4.48 | 20.76 |
| Found | 60.01 | 4.57 | 20.59 |

EXAMPLE 3

3-Cyano-1-methoxycarbonyl-2-(2-pyridylmethylamino)-4H-quinolizin-4-one (S-22)

To a solution of 3.00 g of 3-cyano-1-ethoxycarbonyl-2-(2-pyridylmethylamino)-4H-quinolizin-4-one in 1000 ml of abs. methanol was added 40 mg of sodium hydride and the reaction mixture was heated under reflux for 3 hours. After cooling, the precipitated crystals were collected by filtration to give 2.56 g of 3-cyano-1-methoxycarbonyl-2-(2-pyridylmethylamino)-4H-quinolizin-4-one.

Melting point: 231° C. (decomp.)
IR (KBr): 2200, 1690, 1650, 1620 cm⁻¹
¹H-NMR (DMSO-d₆): δ 4.03(s, 3H), 5.37(d, 2H), 7.33(t, 1H), 7.85–7.96(m, 3H), 8.24(d, 1H), 8.44(d, 1H), 8.87–8.97(m, 2H), 9.05(d, 1H)

| Elementary analysis: C₁₈H₁₄N₄O₃ | | | |
|---|---|---|---|
| | C % | H % | N % |
| Calcd. | 64.67 | 4.22 | 16.76 |
| Found | 64.74 | 4.21 | 16.53 |

EXAMPLE 4

3-Cyano-1-methoxycarbonyl-2-(2-pyridylmethylamino)-4H-quinolizin-4-one hydrochloride (S-23)

3-Cyano-1-methoxycarbonyl-2-(2-pyridylmethylamino)-4H-quinolizin-4-one (1.00 g) was dissolved in 3 ml of concentrated hydrochloric acid and the excess hydrochloric acid was evaporated under reduced pressure. Diethyl ether (50 ml) was added to the residue and the precipitated crystals were collected by filtration to give 1.01 g of 3-cyano-1-methoxycarbonyl-2-(2-pyridylmethylamino)-4H)-quinolizin-4-one hydrochloride.

Melting point: 220° C. (decomp.)
IR (KBr): 2200, 1680, 1645, 1615 cm⁻¹
¹H-NMR (DMSO-d₆): δ 4.04(s, 3H), 5.28(d, 2H), 7.31(t, 1H), 7.69–7.80(m, 3H), 7.95(dt, 1H), 8.20–8.30(m, 2H), 8.86(d, 1H), 9.05(d, 2H)

| Elementary analysis: C₁₈H₁₅N₄O₃Cl | | | |
|---|---|---|---|
| | C % | H % | N % |
| Calcd. | 58.31 | 4.08 | 15.51 |
| Found | 58.35 | 4.04 | 15.59 |

EXAMPLE 5

3-Cyano-2-cyclohexylamino-1-ethoxycarbonyl-4H-quinolizin-4-one (S-24)

To a solution of 288 mg of 3-cycano-1-ethoxycarbonyl-2-methylthio-4H-quinolizin-4-one in acetonitrile, was added 1.14 ml of cyclohexylamine and the reaction mixture was stirred for 4 hours at room temperature. The solvent was evaporated and the residue was triturated with methanol. The crude crystals were recrystallized from dichloromethane-methanol to give 210 mg of 3-cyano-2-cyclohexylamino-1-ethoxycarbonyl-4H-quinolizin-4-one.

Melting point: 140°–141° C.
IR (KBr): 2200, 1675, 1630 cm$^{-1}$
$^1$H-NMR (CDCl$_3$): δ 1.20–1.83(m, 11H), 2.16(br, 2H), 4.44(q, 2H), 4.50(m, 1H), 6.90(t, 1H), 7.51(dt, 1H), 8.21(d, 1H), 8.89(br, 1H), 9.08(d, 1H)

| Elementary analysis: C$_{19}$H$_{21}$N$_3$O$_3$ | | | |
|---|---|---|---|
| | C % | H % | N % |
| Calcd. | 67.24 | 6.24 | 12.38 |
| Found | 67.27 | 6.40 | 12.65 |

EXAMPLE 6

The following compounds were obtained according to the same procedure as described in Example 5.

3-Cyano-1-ethoxycarbonyl-2-[2-(1-pyrrolidinyl)ethylamino[-4H-quinolizin-4-one (S-25)

Melting point: 74°–75° C.
IR (KBr): 2220, 1650, 1620 cm$^{-1}$
$^1$H-NMR (CDCl$_3$): δ 1.43(t, 3H), 1.88(br, 4H), 2.65(br, 4H), 2.85(br, 2H), 4.03(br, 2H), 4.45(q, 2H), 6.92(t, 1H), 7.51(t, 1H), 8.21(d, 1H), 8.69(br, 1H), 9.06(d, 1H)

| Elementary analysis: C$_{19}$H$_{22}$N$_4$O$_3$ | | | |
|---|---|---|---|
| | C % | H % | N % |
| Calcd. | 64.39 | 6.26 | 15.81 |
| Found | 64.68 | 6.36 | 15.89 |

3-Cyano-1-(3-phenylpropoxycarbonyl)-2-[2-(1-pyrrolidinyl)ethylamino]-4H-quinolizin-4-one (S-26)

Melting point: 75°–76° C.
IR (KBr): 2220, 1650, 1625 cm$^{-1}$
$^1$H-NMR (CDCl$_3$): δ 1.81(br, 4H), 2.12(m, 2H), 2.62(br, 4H), 2.76(t, 2H), 2.83(br, 2H), 3.99(br, 2H), 4.39(t, 2H), 6.90(t, 1H), 7.16–7.34(m, 5H), 7.50(dt, 1H), 8.18(d, 1H), 8.72(br, 1H), 9.06(d, 1H)

| Elementary analysis: C$_{26}$H$_{28}$N$_4$O$_3$ | | | |
|---|---|---|---|
| | C % | H % | N % |
| Calcd. | 70.25 | 6.35 | 12.60 |
| Found | 70.21 | 6.47 | 12.79 |

3-Cyano-2-cyclopropylmethylamino-1-ethoxycarbonyl-4H-quinolizin-4-one (S-27)

Melting point: 109°–111° C.
IR (KBr): 2205, 1165, 1630 cm$^{-1}$
$^1$H-NMR (CDCl$_3$): δ 0.38(m, 2H), 0.67(m, 2H), 1.17(m, 1H), 1.46(t, 3H), 3.73(m, 2H), 4.46(q, 2H), 6.93(t, 1H), 7.56(dt, 1H), 8.28(d, 1H), 8.86(br, 1H), 9.09(d, 1H)

| Elementary analysis: C$_{17}$H$_{17}$N$_3$O$_3$ | | | |
|---|---|---|---|
| | C % | H % | N % |
| Calcd. | 65.58 | 5.50 | 13.50 |
| Found | 65.56 | 5.37 | 13.31 |

3-Cyano-2-cyclopropylmethylamino-1-(3-phenylpropoxycarbonyl)-4H-quinolizin-4-one (S-28)

Melting point: 92°–94° C.
IR (KBr): 2200, 1660, 1630 cm$^{-1}$
$^1$H-NMR (CDCl$_3$): δ 0.38(m, 2H), 0.65(m, 2H), 1.15(m, 1H), 2.16(m, 2H), 2.78(t, 2H), 3.73(m, 2H), 4.40(t, 2H), 6.95(t, 1H), 7.18–7.36(m, 5H), 7.53(dt, 1H), 8.25(d, 1H), 8.90(br, 1H), 9.09(d, 1H)

| Elementary analysis: C$_{24}$H$_{23}$N$_3$O$_3$ | | | |
|---|---|---|---|
| | C % | H % | N % |
| Calcd. | 71.80 | 5.77 | 10.47 |
| Found | 71.77 | 5.77 | 10.55 |

3-Cyano-1-ethoxycarbonyl-2-(2-piperidinoethylamino)-4H-quinolizin-4-one (S-29)

Melting point: 119°–120° C.
IR (KBr): 2210, 1670, 1625 cm$^{-1}$
$^1$H-NMR (CDCl$_3$): δ 1.42(t, 3H), 1.62(br, 6H), 2.47(br, 4H), 2.62(br, 2H), 3.95(br, 2H), 4.47(q, 2H), 6.89(t, 1H), 7.49(dt, 1H), 8.15(d, 1H), 8.65(br, 1H), 9.04(d, 1H)

| Elementary analysis: C$_{20}$H$_{24}$N$_4$O$_3$ | | | |
|---|---|---|---|
| | C % | H % | N % |
| Calcd. | 65.20 | 6.57 | 15.21 |
| Found | 65.28 | 6.80 | 15.64 |

3-Cyano-1-(3-phenylpropoxycarbonyl)-2-(2-piperidinoethylamino)-4H-quinolizin-4-one (S-30)

Melting point: 110°–111° C.
IR (KBr): 2210, 1705, 1660, 1630 cm$^{-1}$
$^1$H-NMR (CDCl$_3$): δ 1.48(br, 2H), 1.60(br, 4H), 2.13(m, 2H), 2.45(br, 4H), 2.59(br, 2H), 2.77(t, 2H), 3.92(br, 2H), 4.43(t, 2H), 6.89(t, 1H), 7.17–7.35(m, 5H), 7.49(dt, 1H), 8.12(d, 1H), 8.72(br, 1H), 9.04(d, 1H)

| Elementary analysis: C$_{27}$H$_{30}$N$_4$O$_3$ | | | |
|---|---|---|---|
| | C % | H % | N % |
| Calcd. | 70.72 | 6.59 | 12.22 |
| Found | 70.91 | 6.77 | 12.62 |

3-Cyano-1-ethoxycarbonyl-2-(4-tert-butoxycarbonylcyclohexylamino)-4H-quinolizin-4-one (S-31)

Melting point: 148°–149° C.
IR (KBr): 2200, 1720, 1675, 1630 cm$^{-1}$
$^1$H-NMR (CDCl$_3$): δ 1.00–2.21(m, 8H), 1.43(t, 3H), 1.44(brs, 9H), 3.73(t, 2H), 4.44(q, 2H), 6.93(t, 1H), 7.53(dt, 1H), 8.27(d, 1H), 8.97(br, 1H), 9.09(d, 1H)

| Elementary analysis: C$_{24}$H$_{29}$N$_3$O$_5$ | | | |
|---|---|---|---|
| | C % | H % | N % |
| Calcd. | 65.59 | 6.65 | 9.56 |
| Found | 65.45 | 6.18 | 9.24 |

3-Cyano-1-ethoxycarbonyl-2-(2-tetrahydrofurylmethylamino)-4H-quinolizin-4-one (S-32)

Melting point: 87°–89° C.
IR (KBr): 2200, 1700, 1675, 1635 cm$^{-1}$

¹H-NMR (CDCl₃): δ 1.44(t, 3H), 1.60–1.77(m, 1H), 1.91–2.17(m, 3H), 3.73–4.22(m, 5H), 4.45(q, 2H), 6.92(t, 1H), 7.35(dt, 1H), 8.27(d, 1H), 8.97(br, 1H), 9.08(d, 1H)

| Elementary analysis: C₁₈H₁₉N₃O₄ | | | |
|---|---|---|---|
| | C % | H % | N % |
| Calcd. | 63.33 | 5.61 | 12.31 |
| Found | 63.21 | 5.56 | 12.29 |

3-Cyano-1-ethoxycarbonyl-2-(2,2,6,6-tetramethyl-piperidin-4-ylamino)-4H-quinolizin-4-one (S-33)

Melting point: 89°–91° C.
IR (KBr): 2210, 1670, 1630 cm⁻¹
¹H-NMR (CDCl₃): δ 0.87–1.27(m, 18H), 1.87(m, 2H), 4.14(q, 2H), 4.69(m, 1H), 6.63(t, 1H), 7.24(dt, 1H), 7.93(d, 1H), 8.45(d, 1H), 8.78(d, 1H)

| Elementary analysis: C₂₂H₂₈N₄O₃ | | | |
|---|---|---|---|
| | C % | H % | N % |
| Calcd. | 66.65 | 7.12 | 14.13 |
| Found | 66.18 | 7.11 | 14.11 |

3-Cyano-1-ethoxycarbonyl-2-morpholinoamino-4H-quinolizin-4-one (S-34)

Melting point: 179°–181° C.
IR (KBr): 2210, 1710, 1675, 1635 cm⁻¹
¹H-NMR (CDCl₃): δ 1.46(t, 3H), 2.75(br, 2H), 3.07(br, 2H), 3.89(br, 4H), 4.46(q, 2H), 7.00(t, 1H), 7.60(dt, 1H), 8.27(br, 1H), 9.16(d, 1H), 9.35(br, 1H)

| Elementary analysis: C₁₇H₁₈N₄O₄ | | | |
|---|---|---|---|
| | C % | H % | N % |
| Calcd. | 59.64 | 5.30 | 16.37 |
| Found | 59.94 | 5.34 | 15.78 |

3-Cyano-1-ethoxycarbonyl-2-(4-piperidinylmethylamino)-4H-quinolizin-4-one (S-35)

Melting point: 84°–85° C.
IR (KBr): 2210, 1660, 1630 cm⁻¹
¹H-NMR (CDCl₃): δ 1.19–1.38(m, 2H), 1.46(t, 3H), 1.85(br, 4H), 2.68(t, 2H), 3.18(d, 2H), 3.75(t, 2H), 4.45(q, 2H), 6.95(t, 1H) 7.55(dt, 1H), 8.27(d, 1H), 9.05(br, 1H), 9.09(d, 1H)

| Elementary analysis: C₁₉H₂₂N₄O₃ | | | |
|---|---|---|---|
| | C % | H % | N % |
| Calcd. | 64.39 | 6.26 | 15.81 |
| Found | 64.30 | 6.58 | 16.00 |

3-Cyano-1-ethoxycarbonyl-2-(1-indanylamino)-4H-quinolizin-4-one (S-36)

Melting point: 195°–196° C.
IR (KBr): 2200, 1670, 1650, 1630 cm⁻¹
¹H-NMR (CDCl₃): δ 1.29(t, 3H), 2.13(m, 1H), 2.82–3.14(m, 3H), 4.34(q, 2H), 6.08(q, 1H), 6.95(t, 1H), 7.21–7.39(m, 4H), 7.54(dt, 1H), 8.26(d, 1H), 8.98(d, 1H), 9.12(d, 1H)

| Elementary analysis: C₂₂H₁₉N₃O₃ | | | |
|---|---|---|---|
| | C % | H % | N % |
| Calcd. | 70.76 | 5.13 | 11.25 |
| Found | 70.37 | 5.15 | 10.95 |

3-Cyano-1-ethoxycarbonyl-2-(1,2-diethylpyrazolidin-4-ylamino)-4H-quinolizin-4-one (S-37)

Melting point: 80°–82° C.
IR (KBr): 2195, 1675, 1650, 1625 cm⁻¹
¹H-NMR (CDCl₃): δ 1.12(t, 6H), 1.45(t, 3H), 2.73(m, 4H), 3.01(dd, 2H), 3.45(dd, 2H), 4.46(q, 2H), 5.19(m, 1H), 6.96(t, 1H), 7.56(dt, 1H), 8.26(d, 1H), 9.09(d, 1H), 9.20(d, 1H)

| Elementary analysis: C₂₀H₂₅N₅O₃ | | | |
|---|---|---|---|
| | C % | H % | N % |
| Calcd. | 62.65 | 6.57 | 18.26 |
| Found | 62.59 | 6.64 | 17.82 |

TEST EXAMPLE

Determination of Igs produced in in vitro culture

BALB/c mice were immunized intraperitoneally with 5 μg of DNP-As adsorbed on 4 mg aluminum hydroxide gel Four weeks after the immunization, the spleens were excised from the mice and $5 \times 10^7$ spleen cells were transferred intravenously into the recipient mice which had been exposed to 600 rad of X-ray irradiation. Immediately after cell transfer, the recipients were then immunized intraperitoneally with 5 μg of DNP-As adsorbed on 4 mg aluminum hydroxide gel to induce adoptive secondary immune response. Further 4 weeks after the immunization of recipients, the spleens were excised from them and the spleen cell suspensions containing $5 \times 10^6$ cells/ml were cultured with or without a compound to be tested in 96-well micro-titer plates at 37° C. for 4 days. IgE and IgG secreted into the culture supernatant was each determined correspondingly by ELISA and the inhibitory effect was calculated according to the following equation.

$$\text{inhibition \%} = \frac{\text{average amount of Ig in control group} - \text{average amount of Ig in test group}}{\text{average amount of Ig in control group}} \times 100$$

The results obtained were shown below:

| Comp. No. | Concentration (μg/ml) | Inhibition % of IgE | Inhibition % of IgG |
|---|---|---|---|
| S-1 | 20 | 60 | 13 |
| S-6 | 20 | 68 | 16 |
| S-14 | 10 | 72 | 1 |
| S-15 | 10 | 73 | 3 |
| S-16 | 20 | 68 | 7 |
| S-17 | 10 | 68 | 12 |

What is claimed is:
1. 4H-quinolizin-4-one compound corresponding to the formula:

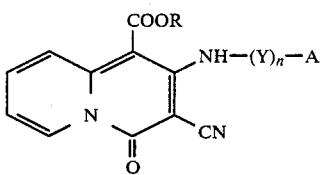

where R is a $C_1$–$C_6$ alkyl group or a $C_7$–$C_{12}$ phenylalkyl group; Y is a $C_1$–$C_6$ alkylene group; n is zero or 1; and A is a cyclic structure selected from the group consisting of pyridyl, pyrimidinyl, pyrazinyl, furyl, tetrahydrofuryl, thienyl, thiazolyl, pyrrolyl, pyrrolidinyl, imidazolyl, pyrazolidinyl, piperidinyl, morpholinyl, indanyl, cyclopropyl and cyclohexyl.

2. 4H-quinolizin-4-one compound corresponding to the formula:

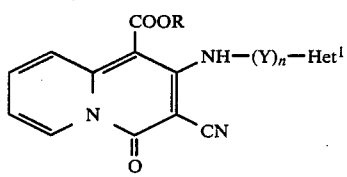

were R is a $C_1$–$C_6$ alkyl group or a $C_7$–$C_{12}$ phenylalkyl group; Y is a $C_1$–$C_6$ alkylene group; n is zero or one; and Het$^1$ is an aromatic heterocyclic structure selected from the group consisting of pyridyl, pyrimidinyl and pyrazinyl.

3. 4H-quinolizin-4-one compound corresponding to the formula:

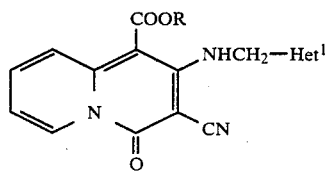

where R is a $C_1$–$C_6$ alkyl group or a $C_7$–$C_{12}$ phenylalkyl group; and Het$^1$ is an aromatic heterocyclic structure selected from the group consisting of pyridyl, pyrimidinyl and pyrazinyl.

4. 4H-quinolizin-4-one compound corresponding to the formula:

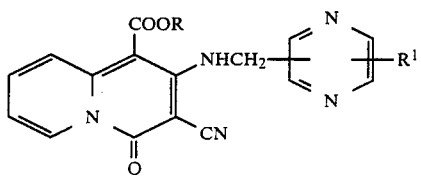

where R is a $C_1$–$C_6$ alkyl group or a $C_7$–$C_{12}$ phenylalkyl group; $R^1$ is a hydrogen atom or a $C_1$–$C_6$ alkyl group.

5. 4H-quinolizin-4-one compound corresponding to the formula:

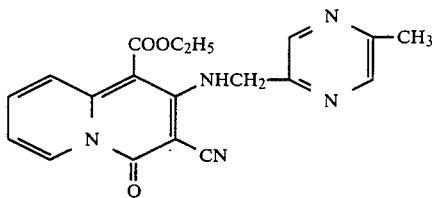

6. 4H-quinolizin-4-one derivatives selected from the group consisting of 3-cyano-1-ethoxycarbonyl-2-(2-pyridylmethylamino)-4H-quinolizin-4-one; 3-cyano-1-ethoxycarbonyl-2-[2-(2-pyridyl)ethylamino]-4H-quinolizin-4-one; 3-cyano-1-(3-phenylpropoxycarbonyl)-2-[2-(2-pyridyl)ethylamino]-4H-quinolizin-4-one; 3-cyano-1-ethoxycarbonyl-2-(2-furylmethylamino)-4H-quinolizin-4-one; 3-cyano-2-(2-furylmethylamino)-1-(3-phenylpropoxycarbonyl)-4H-quinolizin-4-one; 3-cyano-1-ethoxycarbonyl-2-(3-pyridylmethylamino)-4H-quinolizin-4-one; 3-cyano-1-ethoxycarbonyl-2-(4-pyridylmethylamino)-4H-quinolizin-4-one; 3-cyano-1-ethoxycarbonyl-2-[2-(4-methylthiazol-5-yl)-ethylamino]-4H-quinolizin-4-one; 3-cyano-1-ethoxycarbonyl-2-thienylmethylamino-4H-quinolizin-4-one; 3-cyano-1-ethoxycarbonyl-2-(3-thienylmethylamino)-4H-quinolizin-4one; 3-cyano-1-ethoxycarbonyl-2-(2-thienylethylamino)-4H-quinolizin-4-one; 3-cyano-1-ethoxycarbonyl-2-[2-(3-thienyl)ethylamino-4H-quinolizin-4-one; 2-(4-amino-2-methylpyrimidin-5-yl)-methylamino-3-cyano-1-ethoxycarbonyl-4H-quinolizin-4-one; 3-cyano-1-ethoxycarbonyl-2-pyrazinylmethylamino-4H-quinolizin-4-one; 3-cyano-1-ethoxycarbonyl-2-(3-methylpyrazinyl)-methylamino-4H-quinolizin-4-one; 3-cyano-1-ethoxycarbonyl-2-(5-methylpyrazinyl)methylamino-4H-quinolizin-4-one; 3-cyano-1-ethoxycarbonyl-2-(6-methylpyrazinyl)methylamino-4H-quinolizin-4-one; 3-cyano-1-ethoxycarbonyl-2-[2-(5-nitropyridin-2-ylamino)ethylamino]-4H-quinolizin-4-one; 3-cyano-1-ethoxycarbonyl-2-[2-(1-methylpyrrol-2-yl)-ethylamino]-4H-quniolizin-4-one; 3-cyano-1-ethoxycarbonyl-2-imidazolylmethylamino-4H-quinolizin-4-one; 3-cyano-1-ethoxycarbonyl-2-(4-imidazolylmethylamino)-4H-quinolizin-4-one; 3-cyano-1-methoxycarbonyl-2-(2-pyridylmethylamino)-4H-quinolizin-4-one; 3-Cyano-1-methoxycarbonyl-2-pyridylmethylamino)-4H-quinolizin-4-one hydrochloride; 3-cyano-2-cyclohexylamino-1-ethoxycarbonyl-4H-quinolizin-4-one; 3-cyano-1-ethoxycarbonyl-2-[2-(1-pyrrolidinyl)ethylamino]]-4H-quinolizin-4-one; 3-cyano-1-(3-phenylpropoxycarbonyl)-2[2-(1-pyrrolidinyl)-ethylamino]-4H-quinolizin-4-one; 3-cyano-2-cyclopropyl-methylamino-1-ethoxycarbonyl-4H-quinolizin-4-one; 3-cyano-2-cyclopropylmethylamino-1-(3-phenylpropoxycarbonyl)-4H-quinolizin-4-one; 3-cyano-1-ethoxycarbonyl-2-(2-piperidinoethylamino)-4H-quinolizin-4-one; 3-cyano-1-(3-phenylpropoxycarbonyl)-2-(2-piperidinoethylamino-4H-quinolizin-4-one; 3-cyano-1-ethoxycarbonyl-2-(4-tert-butoxycarbonylcyclohexylamino)-4H-quinolizin-4-one; 3-cyano-1-ethoxycarbonyl-2-(2-tetrahydrofurylmethylamino)-4H-quinolizin-4-one; 3-cyano-1-ethoxycarbonyl-2-(2,2,6,6-tetramethylpiperidin-4-ylamino)-4H-quinolizin-4-one; 3-cyano-1-ethoxycarbonyl-2-morpholinoamino-4H-quinolizin-4-one; 3-cyano-1-ethoxycarbonyl-2-(4-piperidinylmethylamino)-4H-quinolizin-4-one; 3-cyano-1-ethoxycarbonyl-2-(1-indanylamino)-4H-quinolizin- 4-one; and 3-cyano-1-ethoxycarbonyl-2-(1,3-diethylpyrazolidin-4-ylamino)-4H-quinolizin-4-one.

7. A method for the treatment of allergic bronchial asthma, allergic rhinitis, atopic dermatitis and other hypersensitiveness diseases associated with immunoglobulin E-antibody formation in a mammal which comprises administering an effective dosage from about 0.1 mg to 10 mg per kg of mammal weight by oral administration or from about 0.02 mg to 5 mg per kg of mammal weight by parenteral administration per day of an immunoglobulin E-antibody formation-inhibiting 4H-quinolizin-4-one compound to the mammal; wherein the 4H-quinolizin-4-one compound corresponds to a formula in accordance with claim 1, or a pharmaceutically acceptable salt thereof.

8. A pharmaceutical composition for the treatment of allergic bronchial asthma, allergic rhinitis, atopic dermatitis and other hypersensitiveness diseases associated with immunoglobulin E-antibody formation in a mammal, which composition contains an effective dosage from about 0.1 mg to 10 mg per kg of mammal weight for oral administration or from about 0.02 mg to 5 mg per kg of mammal weight for parenteral administration per day of an immunoglobulin E-formation-inhibiting 4H-quinolizin-4-one compound; wherein the 4H-quinolizin-4-one compound corresponds to a formula in accordance unit claim 1, or a pharmaceutically acceptable salt thereof.

9. A method of accordance with claim 7 wherein the 4H-quinolizin-4-one compound is 3-cyano-1-ethoxycarbonyl-2-(5-methylpyrazinyl)methylamino-4H-quinolizin-4-one or 3-cyano-1-propoxycarbonyl-2-(3-pyridyl)methylamino-4H-quinolizin-4-one.

* * * * *